United States Patent
Prasad et al.

(10) Patent No.: US 7,640,175 B1
(45) Date of Patent: Dec. 29, 2009

(54) METHOD FOR HIGH-RISK MEMBER IDENTIFICATION

(75) Inventors: Badri N. Prasad, Richfield, MN (US); Archelle Georgiou, Eden Prairie, MN (US); Gerald L. Lutgen, St. Paul, MN (US)

(73) Assignee: Ingenix, Inc., Eden Prairie, MN (US)

( * ) Notice: Subject to any disclaimer, the term of this patent is extended or adjusted under 35 U.S.C. 154(b) by 693 days.

(21) Appl. No.: 09/733,215

(22) Filed: Dec. 8, 2000

(51) Int. Cl.
G06Q 40/00 (2006.01)

(52) U.S. Cl. .............................................. 705/3; 705/4

(58) Field of Classification Search ................ 705/2–4, 705/1, 35, 38, 8, 10, 5; 435/7.1; 706/21; 600/300, 310, 345
See application file for complete search history.

(56) References Cited

U.S. PATENT DOCUMENTS

| | | | | |
|---|---|---|---|---|
| 5,365,425 A * | 11/1994 | Torma et al. | ................... | 705/2 |
| 5,486,999 A * | 1/1996 | Mebane | ........................ | 705/2 |
| 5,498,524 A * | 3/1996 | Hall | ........................... | 435/7.1 |
| 5,619,990 A * | 4/1997 | Kanai | ........................ | 600/300 |
| 5,706,441 A | 1/1998 | Lockwood | | |
| 5,752,236 A * | 5/1998 | Sexton et al. | .................. | 705/4 |
| 5,835,897 A | 11/1998 | Dang | | |
| 5,845,254 A * | 12/1998 | Lockwood et al. | ............. | 705/2 |
| 5,924,073 A * | 7/1999 | Tyuluman et al. | ............. | 705/2 |
| 5,940,802 A * | 8/1999 | Hildebrand et al. | ........... | 705/3 |
| 5,970,463 A | 10/1999 | Cave et al. | | |
| 5,976,082 A * | 11/1999 | Wong et al. | ................. | 600/300 |
| 6,163,770 A * | 12/2000 | Gamble et al. | ................ | 705/4 |
| 6,363,393 B1 * | 3/2002 | Ribitzky | .................... | 707/102 |
| 6,370,511 B1 | 4/2002 | Dang | | |
| 6,385,589 B1 * | 5/2002 | Trusheim et al. | ............... | 705/2 |
| 6,456,979 B1 * | 9/2002 | Flagg | .......................... | 705/4 |
| 6,470,320 B1 * | 10/2002 | Hildebrand et al. | ........... | 705/3 |
| 6,484,144 B2 * | 11/2002 | Martin et al. | .................. | 705/2 |

(Continued)

FOREIGN PATENT DOCUMENTS

CA 2216681 * 3/1998

(Continued)

OTHER PUBLICATIONS

"Looking to manage care more closely. (new technique in case management to manage chronic illness and high- risk pregnancies)", Shoor, Rita, Business & Health, v11, n10, p. 46 (6), Sep. 1993, Dialog File 149, Acc. No. 01429566.*

(Continued)

Primary Examiner—Gerald J. O'Connor
Assistant Examiner—Natalie A. Pass
(74) Attorney, Agent, or Firm—Adriana S. Luedke; Dorsey & Whitney LLP

(57) ABSTRACT

A method for using claims data to identify high-risk members of a healthcare plan is disclosed. In one embodiment, the present invention includes searching the plurality of claims of members selected by a filtering criteria to identify the presence of an intervention flag, to identify factors influencing care intervention, and identifying a medical episode driving the member's cost. In one embodiment, the intervention flag the medical episode are displayed in association with an identification of the member. In another embodiment, the member selection criteria includes selection based on the member's predicted future health care utilization.

2 Claims, 9 Drawing Sheets

U.S. PATENT DOCUMENTS

| | | | |
|---|---|---|---|
| 6,578,003 B1* | 6/2003 | Camarda et al. | 705/3 |
| 6,581,204 B2 | 6/2003 | DeBusk et al. | |
| 6,587,829 B1* | 7/2003 | Camarda et al. | 705/3 |
| 6,629,095 B1 | 9/2003 | Wagstaff et al. | |
| 6,802,810 B2 | 10/2004 | Clarniello et al. | |
| 2001/0020229 A1* | 9/2001 | Lash | 705/3 |
| 2001/0029322 A1* | 10/2001 | Iliff | 600/300 |
| 2002/0004725 A1* | 1/2002 | Martin et al. | 705/2 |
| 2002/0095316 A1* | 7/2002 | Toan et al. | 705/4 |
| 2002/0111826 A1* | 8/2002 | Potter et al. | 705/2 |
| 2003/0167189 A1* | 9/2003 | Lutgen et al. | 705/3 |
| 2004/0024620 A1* | 2/2004 | Robertson et al. | 705/4 |
| 2004/0049408 A1* | 3/2004 | Voss et al. | 705/3 |
| 2004/0199332 A1 | 10/2004 | Iliff | |

FOREIGN PATENT DOCUMENTS

| | | | |
|---|---|---|---|
| EP | 0917078 A1 * | 5/1999 | |
| WO | WO 99/44167 | 9/1999 | |

OTHER PUBLICATIONS

"A Chronic Disease Score with Empirically Derived Weights" Daniel Clark et al. ,Medical Care, vol. 33, No. 8, pp. 783-795, 1995 Lippincott Raven publishers.*

Alexandre, Leslie M., "High-Cost Patients in a Fee-For-Service Medical Plan, The Case for Earlier Intervention," *Medical Care*, Feb. 1990, vol. 28, No. 2, pp. 112-123.

Clark, Daniel O., et al., "A chronic Disease Score with Empirically Derived Weights," *Medical Care*, vol. 33, No. 8, pp. 783-795.

Roblin, Douglas W., et al., "A Low-Cost Approach to Prospective Identification of Impending High-Cost Outcomes," *Medical Care*, vol. 37, No. 11, pp. 1155-1163.

Steen, Paul M., "Approaches to Predictive Modeling," Ann Thorac Surg 1994:58:1836-40.

Imagine If You Could Obtain Accurate Clinical Data From The Point Of Care. MD Trends Web Site. Dec. 4, 2000. [Retrieved on Nov. 3, 2002]. Retrieved from the internet:< URL: http://web.archive.org/web/20001204191600/www.mdtrends.com/>.

* cited by examiner

30

Filter Member List

Member Selection

Specify criteria for member selection (joins allowed, excluding rank):

32 — ☐ Relative risk RANK is between [1] and [100]
    *(Highest risk is ranked as 1)*

34 — ☐ Relative Risk between [0] and [10]
36 — ☐ Disease category
       Selection detail: [List...]
38 — ☐ Residential zip code: [List...]
40 — ☐ County name: [List...]
       ☐ Product: [List...]
42 — ☐ Group Number: [List...]
44 — ☐ Member name (specify string): [          ]
46 — ☐ Member ID (specify string): [          ]

[>> Next >>]                    [Exit >]

Member Information

Demographics and Utilization:

- Member name: Member Name
- Address: Member Address
- Age: 50
- Gender: F
- Phone: Member Phone
- Member ID: 6546841284694200
- Ratio of out of network cost to total cost: 10%
- Past year total cost: $23,515
- Predicted total cost: $20,700
- ER visits in past year: 3

Risk Factors: Information in blue can be right-clicked for more detail.

- Relative risk: 16.6
- Intervenability: 8
- Behavioral & MH diagnoses: Yes
- Self care characteristics: Yes
- Equipment/Monitors: No
- Drug history: Yes

Top episode categories driving risk:
- Neoplasms of the breast and female reproductive system
- Affective disorders [depressive disorders]
- Sleep disorders
- Obstructive pulmonary diseases [diseases which narrow airways or re...]

Record: 1 of 4

Right-click a category to view episode classes

[View All Episodes]  [<< Back <<]  [Exit]

| | | Member Name | | |
|---|---|---|---|---|
| 132 | 134 | Drug History Report | 136 | 138 |
| | | Pharmacy | | |
| Drug Category | Date Filled | NDC Code | Drug Name | |
| Analgesics,narcotics | 8/23/1999 | 00378115505 | Propoxyphene napsylate w/apap | |
| | 8/8/1999 | 00378115505 | Propoxyphene napsylate w/apap | |
| | 8/2/1999 | 00378115505 | Propoxyphene napsylate w/apap | |
| | 7/26/1999 | 00378115505 | Propoxyphene napsylate w/apap | |
| | 7/21/1999 | 00603388421 | Hydrocodone w/acetaminophen | |
| | 7/15/1999 | 00054465029 | Roxicet | |
| | 7/10/1999 | 00054465029 | Roxicet | |
| | 7/6/1999 | 00054465029 | Roxicet | |
| | 7/3/1999 | 00054465029 | Roxicet | |
| | 6/25/1999 | 00603388421 | Hydrocodone w/acetaminophen | |
| | 6/15/1999 | 00603388128 | Hydrocodone w/acetaminophen | |
| | 3/18/1999 | 52544034901 | Hydrocodone w/acetaminophen | |
| Anti-anxiety drugs | 12/14/1999 | 00228205950 | Lorazepam | |
| Anti-emetics | 12/8/1999 | 00378510501 | Prochlorperazine maleate | |
| | 12/8/1999 | 00008021201 | Phenergan | |
| | 11/15/1999 | 00378510501 | Prochlorperazine maleate | |
| | 10/21/1999 | 00008021201 | Phenergan | |

FIG. 9

METHOD FOR HIGH-RISK MEMBER IDENTIFICATION

CROSS-REFERENCE TO RELATED APPLICATION(S)

None.

BACKGROUND OF THE INVENTION

The present invention relates to a system and method for identifying high-risk members in a healthcare plan. More particularly, it relates to a system and method for using information from physician claims, facility claims, and pharmacy claims to identify high-risk members in a healthcare plan and to provide salient information on those members to an intervention agent.

For the past few decades, the predominant model of healthcare management used by most health care plans in the managed care industry has been one that focuses primarily on approving or denying coverage for medical procedures based upon specially developed criteria. This system has been subject to some criticism from doctors who feel that their treatment decisions should not be questioned, and from patients who feel that their health care plan places undue emphasis on financial consequences at the expense of sound medical care. Further, the current model employed by health care plans fails to place the appropriate amount of emphasis on proactive care. Studies have shown that an emphasis on proactive care can improve a health care plan member's overall health and well-being. Proactive care can also reduce the overall expense to a health care plan by replacing expensive medical procedures and treatments with less expensive proactive care activities.

Finally, under the current model, plan members commonly have minimal or no positive contact with their health care plan. Members pay health care premiums individually or through their employer and hope that, when treatment is needed, the health care plan will approve coverage. There is a need in the art for a health care management model that addresses the above shortcomings of the predominant current model. To implement a proactive-care-based or interventional model that allows a healthcare plan to take a proactive approach to providing health care to its members, it is necessary to have an effective system of identifying high-risk plan members or identifying plan members that are amenable to intervention (i.e., those members who can be helped with proactive or interventional care) and compiling relevant information regarding those members.

When a member of a health care plan receives care from health care providers, information regarding the care received is provided to plan administrators in documents commonly referred to as claims. Predominantly, this information is provided in the following three types of claims: physician claims, facility claims, and pharmacy claims. These claims are the documents that are submitted to the health care plan by physicians, hospitals, and pharmacies to receive reimbursement for care provided to the plan member. These documents generally contain coded data that provides information regarding the care received by the plan member. These claims are processed by the health care plan, and where appropriate, payment is transmitted to the health care provider.

For purposes of this specification, the phrase "physician claim" is used to refer to any professional service claim submitted to a health plan, typically on an HCFA-1500 form or its equivalent, and the phrase "facility claim" is used to refer to any facility claim. The phrase "medical claim" is used to refer to both physician claims and facility claims. Finally, the phrase "pharmacy claim" is used to refer to any claim submitted by a pharmacy or durable medical goods provider. Medical claims generally include codes for diagnoses and procedures relating to the plan member. The reason for the visit is typically represented by an International Classification of Diseases ("ICD") code, currently in its ninth revision and thus commonly referred to as "ICD-9." The description of the service provided in a medical claim typically takes one of two formats, a Common Procedural Terminology ("CPT") code (promulgated by the American Medical Association), or a Health Care Procedural Code ("HCPC") (promulgated by the Health Care Financing Administration).

The following materials serve as background for the present application and provide further information on some of the classification systems discussed: *Physician's Current Procedure Terminology*, CPT '94, published by the American Medical Association; HCPCS 1994 *Medicare's National Level II Codes*, published by Medicode, Inc.; Med-Index *ICD9 CM Fourth Edition* 1993, published by Med-Index, each of which is hereby incorporated by reference in its entirety.

BRIEF SUMMARY OF THE INVENTION

In one embodiment, the present invention is a method for identifying intervention flags, from a plurality of claims, for a member of a healthcare plan. The method includes searching the plurality of claims to identify the presence of an intervention flag and generating a display showing the intervention flag in association with an identification of the member.

Still other embodiments of the present invention will become apparent to those skilled in the art from the following detailed description, wherein is shown and described only the embodiments of the invention by way of illustration of the best modes contemplated for carrying out the invention. As will be realized, the invention is capable of modification in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2 shows an exemplary screen display of a member selection screen, according to one embodiment of the present invention.

FIG. 3 shows an exemplary screen display of a member assignment screen, according to one embodiment of the present invention.

FIG. 4 shows an exemplary screen display of a member information screen, according to one embodiment of the present invention.

FIG. 8 shows an exemplary screen display of a behavioral risk factors screen, according to one embodiment of the present invention.

FIG. 9 shows an exemplary screen display of a drug history report screen, according to one embodiment of the present invention.

DETAILED DESCRIPTION

Figure 1:
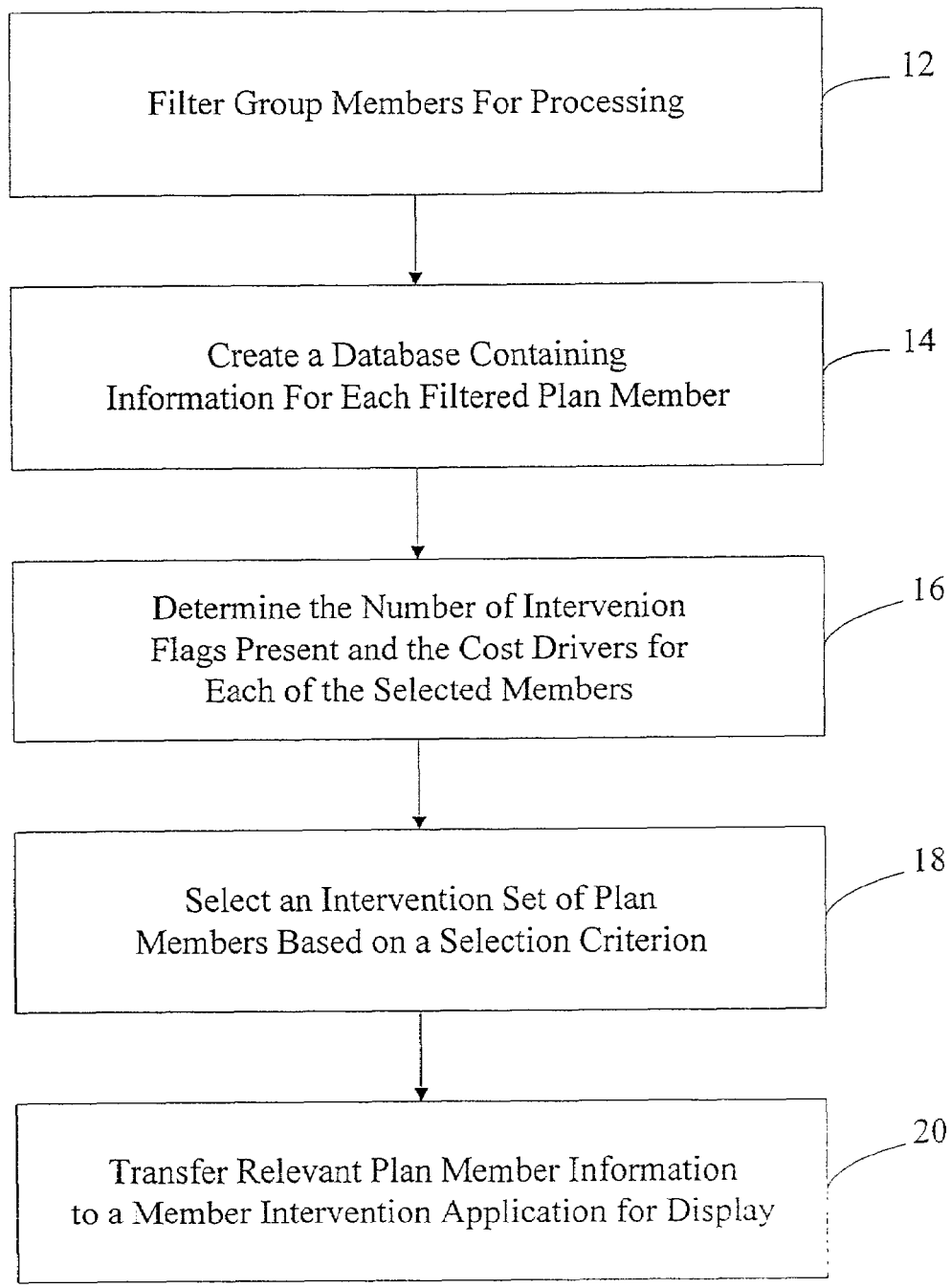
FIG. 1 is a block diagram illustrating the high-risk member identification method, according to one embodiment of the present invention.

FIG. 1 is a block diagram illustrating the high-risk member identification method of the present invention. As shown in FIG. 1, generally the high-risk member identification method 10 includes filtering members of a group for processing (block 12), creating a database containing information for each plan member (block 14), determining which intervenability factors are present for a member and determining the cost drivers for the member (block 16), selecting members based on a selection criterion (block 18), and transferring relevant plan member information to a member intervention application for display to an intervention agent (block 20). The term "intervention agent" is used throughout this specification to refer to the individual that examines the information presented in the display for a given member and attempts to proactively intervene in that member's medical care. Each of these aspects of the present invention will be described in further detail below.

As shown in bock 12, in one embodiment, the high-risk member identification method 10 involves filtering members from a group or plan for processing. In other words the entire group is filtered according to a filter criterion to generate a subset of the group for processing by the present method. In one embodiment of the present invention, the members are filtered based on exceeding a threshold for actual or predicted future healthcare resource utilization. In another embodiment, the top five percent of the group members are chosen for further analysis. In another embodiment of the present invention, where a relative risk is calculated for each member of the group, the members are filtered based on exceeding a threshold for relative risk. In another embodiment, the top five percent of the group members by relative risk are chosen for further analysis. In another embodiment, any given member is chosen for any reason for further analysis. For example, a given group member may request that his or her claims history be examined for potential intervention flags. In another embodiment of the present invention, all members of the group are chosen for further analysis.

As shown in block 14, information is then collected on each chosen member's medical diagnoses and health care utilization patterns over a specified time period. In one embodiment, this information is collected or compiled from claims data, including physician claims, facility claims, and pharmacy claims. The specified time period over which this information is collected for each member of a health care plan is referred to as the "focus period." In one embodiment, the focus period is one year. In other embodiments, the focus period may be longer or shorter.

As explained above, medical claims typically include information on medical diagnoses and treatments provided to the member. Typical fields included in physician claims, facility claims, and pharmacy claims are generally known to those of skill in the art. In one embodiment of the present invention, the important fields that are extracted from a physician claim, to generate the database, include the date of service, the physician provider identification, the reason for the visit, and a description of the service or services provided. In one embodiment of the present invention, the important fields in a facility claim include the date of service, the facility provider identification, the reason for the visit, and a description of the services provided. In one embodiment of the present invention, the important fields in a pharmacy claim include the date of fill, the pharmacy provider identification, the prescribing physician provider identification, and the description of the medication, generally in the form of a National Drug Code ("NDC").

One exemplary specification for extracting information from the claims data for each member of the health care plan during the focus period is described in U.S. patent application Ser. No. 09/635,911, now U.S. Pat. No. 7,444,291, entitled "System and Method for Modeling of Health Care Utilization," by Gerald L. Lutgen et al., filed Aug. 10, 2000, which is hereby incorporated by reference in its entirety. In other embodiments of the present invention, other specifications known to those of skill in the art are used to extract relevant data or information from the medical and pharmacy claims for the focus period to compile the database.

After the members are filtered and the database is compiled, the claims for each of the chosen members are analyzed to determine the number of intervenability factors or flags present for each plan member (block 16). This is performed at this point in the method, because, in one embodiment, the number of intervenability factors is used as one of the selection criteria described below (block 18). Also, performing this determination prior to selecting the intervention set reduces the time needed to generate the information display (block 20), because the necessary processing is performed in advance. In another embodiment, the intervenability factors are not determined prior to selecting (block 18) and thus are not used as one of the selection criteria.

In one embodiment of the present invention, the top medical episodes driving risk for each plan member are also determined at this point in the method (block 16). Again, this is done to reduce the time needed to generate the information display (block 20). In another embodiment, the top medical episodes driving risk are calculated "on-the-fly" or during generation of the information display (block 20). The technique for determining the top medical episodes driving risk is described in more detail below. In one embodiment, all other information generated for each plan member (as shown in FIG. 4) is generated on-the-fly, because it can be ascertained quickly and this approach eliminates the need to generate this information for members eliminated during the selection of the intervention set (block 18).

Intervenability factors are those areas or aspects of a member's care history or patterns that are amenable to intervention by an intervention agent. In other words, they are areas that can be readily identified using claims data, can be corrected or improved, and that are likely to result in a reduction of health care costs or improve the overall health and well-being of the member. In one embodiment of the present invention, the intervenable factors that are assessed for each plan member, to determine if they are present, include: (1) whether the member visited an emergency room during the focus period, (2) whether the member had any in-patient hospital admissions during the focus period, (3) whether the member incurred any out-of-network costs during the focus period, (4) whether the member visited more than three different provider specialists during the focus period, (5) whether the member was prescribed multiple pharmaceuticals during the focus period, (6) whether the member has no appropriate provider for a chronic episode during the focus period, (7) whether the member missed a targeted intervention during the focus period, and (8) whether the member is failing to comply with taking mediations prescribed during the focus period. The claims for a given plan member, in the database, are analyzed to ascertain the presence or absence of each of the intervenability factors. The total number of intervenability factors present for a member is recorded. Each of these intervention factors, and how their presence is determined, is described in more detail below. In other embodiments of the present invention, other intervenability factors are assessed for each plan member. In another embodiment, only one of the intervenability factors identified above is assessed.

In one embodiment of the present invention, a relative risk is calculated and assigned to each selected member. In this embodiment, the relative risk is used as one of the criteria for selecting the intervention set (block 18). In another embodiment, relative risk is used as the basis for making the initial selection, as described in block 12 of FIG. 1. The relative risk ranking is a function of the predicted future health care resource utilization for the member. The predicted future health care utilization is calculated from the claims data in the database. In one embodiment of the present invention, the cost of services provided to the member during the focus period is calculated. This number is then used as the marker for future health care utilization. In another embodiment of the present invention, the predicted future health care utilization is calculated by looking at only the claims information from the medical claims and computing a total cost of services provided during the focus period. In another embodiment of the present invention, future utilization is calculated by examining only data from the pharmacy claims and computing the total cost of pharmacy services provided during the focus period. In another embodiment of the present invention, future utilization is calculated based on chronic medical conditions only for the member during the focus period. In one embodiment of the present invention, the predicted future health care utilization is calculated using one of the techniques disclosed in U.S. patent application Ser. No. 09/635,911, now U.S. Pat. No. 7,444,291, entitled "System and Method for Modeling of Health Care Utilization," identified above and hereby incorporated by reference in its entirety.

In one embodiment, after the predicted future health care utilization cost is calculated, each member is assigned a relative risk, which is that particular member's predicted future health care utilization or cost, divided by the average for the entire group. In other words, the relative risk is basically a number representing a particular member's predicted future health care utilization in relation to the average for the group. In other words, if a given member's relative risk is two, his predicted future health care utilization is twice that of the average.

In one embodiment of the present invention, once a relative risk is assigned to each plan member, the relative risk ranking can be assigned. The relative risk ranking is assigned to each of the selected plan members by assigning the member with the highest relative risk a ranking of "1," the member with the next highest relative risk a ranking of "2," and so on, until every selected member has been assigned a relative risk ranking. In one embodiment, the relative risk ranking serves as yet another criteria for filtering.

As shown in block 18 of FIG. 1, an intervention set of plan members is generated by selecting members according to one or more selection criteria. FIG. 2 is a screen display from a software-based application, for performing the method of the present invention, that allows an intervention agent to select a set of plan members from the group based on certain selection criteria. As shown in FIG. 2, the member selection screen 30 includes boxes that allow the group members to be selected or extracted by relative risk rank 32, relative risk 34, disease category 36, zip code 38, and county 40. In the case of a member information database containing information for multiple employer groups, the member selection screen 30 includes a selection to allow plan members to be extracted by group number 42. The member selection screen 30 also allows members to be searched by member name 44 and member ID 46. As shown in FIG. 2, a user may search for all plan members having relative risk rank between specified numbers. The relative risk rank is assigned as described in detail above. As further shown, the user may also search by relative risk 34 between two specified numbers. The relative risk is determined as explained above.

As also shown, the user may select plan members based on disease category 36. This will select all members having a claim within a specified disease category. In one embodiment of the present invention, the disease categories are ICD-9 codes. In another embodiment of the present invention, the disease categories are Clinical Care Group ("CCG") codes. CCG's are an Ingenix innovation for classifying diagnosis codes and medical claims. The CCG system allows the over 14,000 ICD-9 codes to be placed into a more manageable number of CCG classes, namely, about 450 related disease or diagnosis categories. These approximately 450 CCG classes can be further reduced into about 120 CCG categories. Finally, these approximately 120 CCG categories can be placed into about 20 CCG specialties. Each of these levels provides various advantages in analyzing the claims data.

In one embodiment of the present invention, CCG categories are assigned to each of the pharmacy claims. This process requires that the pharmacy claims be processed together with the medical claims in order to attach a CCG category to each pharmacy claim. In one embodiment, this is accomplished using the Ingenix Drug-Disease Matcher ("DDM") application. This application is described in greater detail in U.S. patent application Ser. No. 09/571,648, filed on May 15, 2000, entitled "SYSTEM AND METHOD OF DRUG-DISEASE MATCHING," by Gerald Lutgen et al. which is hereby incorporated by reference in its entirety.

As further shown in FIG. 2, in another embodiment of the present invention, the member selection screen 30 allows for searching by zip code 38. Searching by zip code 38 allows the user to select a set of plan members in a certain geographic region. This may be beneficial if the user wishes to assign all of these members to a specific intervention agent (as further described below). In another embodiment of the present invention, the member selection screen 30 allows the user to search the database by county name 40. The search by county name 40 is similar to a search by residential zip code 38 in that the user may select a set of plan members based on geographic location. In an embodiment where the member information database includes members from multiple groups, the member selection screen 30 allows the members to be searched by group number 42. This allows the user to select only those members within a specific group. In one embodiment, the member selection screen 30 includes a member name 44 field that allows the user to search for a specific plan member by name. In another embodiment, the member selection screen 30 includes a member ID 46 field that allows the user to select a plan member based on the member's numerical identification.

In one embodiment of the present invention, the user may use the member selection screen 30 to select a set of members from the group by using multiple selection criteria. In one embodiment of the present invention, each of the selection criteria shown in FIG. 2 is present in the member selection screen 30, allowing the user to select an intervention set of members using any of the shown fields. The user may select an intervention set of members by selecting fields it wishes to search and entering appropriate selection information. In other embodiments, only one of the fields shown on the member selection screen 30 is present.

Figure 3:
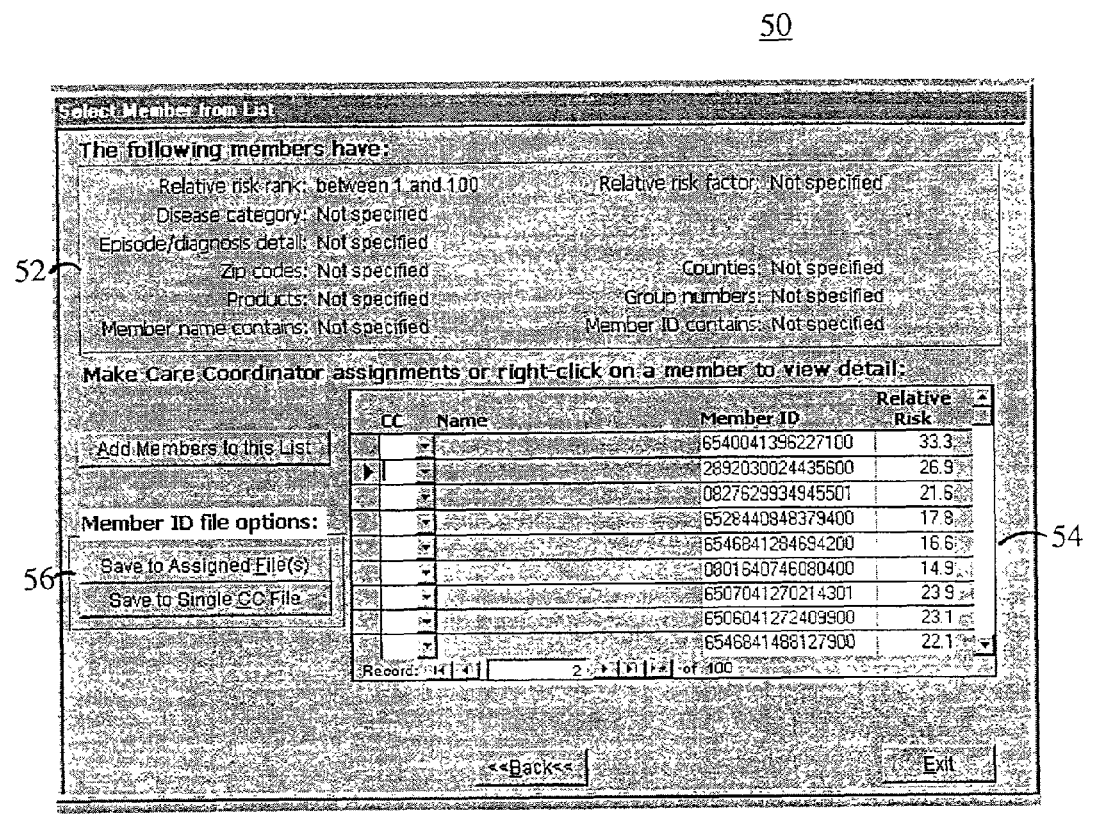

As shown in FIG. 3, the member selection listing 50 includes a search summary section 52, a member listing section 54, and a save-to-file button 56. The member selection listing 50 allows the user (e.g., a care management supervisor) to view the entered selection criteria, using the section 52, and assign an intervention agent to each member in the member listing section 54. The member listing section 54 lists each of the members of the intervention set. Once an intervention agent has been assigned, the user can save the assignments to individual files using the save button 56. The user can then transmit each of these files to the appropriate intervention agent for intervention.

In one embodiment of the present invention, the members of the intervention set are listed according to relative risk rank, with the member having the lowest rank listed first. In one embodiment of the present invention, the members of the intervention set are listed by first sorting the members by relative risk and then further sorting by the number of intervenability factors present for that member, such that within a given relative risk number, the plan members with the highest number of intervenability factors are ranked first, and those with a lower number of intervenability factors are ranked lower. In one embodiment of the present invention, the first step, sorting the members of the intervention set by relative risk, involves placing plan members into a relative risk category based on whole numbers only. In other words, for example, all members having a relative risk of "3" and a fraction are placed into the "3" relative risk category.

In another embodiment of the present invention, the members of the intervention set are assigned a relative risk ranking by first sorting the members according to the number of intervenability factors present for each member. In other words, all members having eight intervenability factors present are placed at the top of the list, all members having seven intervenability factors are placed second, and so on. Next, within each number of intervenability factors, members are ranked according to relative risk, with the member having the highest relative risk placed first. In other embodiments of the present invention, some other formula is used to order the members of the intervention set based on some combination of the member's relative risk and the member's intervenability factors. The specific formula used to order members is not important, but the idea is to rank the members of the intervention set according to those who most need intervention and those who are most amenable to intervention.

As shown in block 20 of FIG. 1, a display is generated containing relevant information regarding the plan member. This display is used by the intervention agent to intervene in the member's care. The display is generated when the intervention agent selects a particular member. FIG. 4 shows the member information screen 60, according to one embodiment of the present invention. The member information screen 60 provides the intervention agent with information regarding a particular plan member that assists the agent in determining where the plan member would benefit from intervention in care. In one embodiment of the present invention the display only includes that information previously discussed. In another embodiment of the present information, further information is now extracted from the claims for the particular member, as discussed below.

As shown in FIG. 4, in one embodiment, the member information screen 60 includes a demographic information section 62, a utilization summary 64, and a "risk factors" section 66. In one embodiment, the demographic information includes the member's name, address, age, gender, phone number, and identification number. In the embodiment shown in FIG. 4, the utilization summary 64 includes an indication of the amount of out-of-network costs incurred by the member, a total health care cost for the member in the past year (or some other historic period), a predicted total cost for an upcoming time period, and the number of emergency room visits in the past year (or some other time period).

The "risk factors" section 66 of the member information screen 60 provides information used by the intervention agent to intervene in the member's health care treatment strategy. As shown in FIG. 4 on the left hand side, the "risk factors" section 66 includes information regarding relative risk 68 and intervenability 70. The section also includes information on other factors influencing care intervention, including mental health diagnoses 72, self-care characteristics 74, equipment or monitors 76, and drug history 78. On the right hand side, the "risk factors" section 66 includes a top medical episode categories section 79. The top medical episode categories section 79 identifies the top medical episode categories that are driving risk and future health care resource utilization for the current plan member. In one embodiment of the present invention, only intervenability 70 is present in the "risk factors" section 66. In another embodiment, only intervenability 70 is present.

The member demographic information 62 is extracted from the information in the database extracted from the claims data. The information in the utilization summary section 64 is likewise extracted from the database including claims information, with the exception of the predicted total cost. The predicted total cost is calculated as described above with reference to predicted future health care utilization. The predicted total cost may be computed using those methods described herein or any methods known to those of skill in the art.

Relative risk 68 is computed as described above and displayed in the member information screen 60 to give the intervention agent a quick summary of the current plan member's level of risk. The entry for intervenability 70 is the number of intervenability factors present for the current member. The entry for mental health diagnoses 72, in the embodiment of the invention shown in FIG. 4, is a "yes" or "no" entry. A "yes" is entered for mental health diagnoses 72 if an examination of the physician claims for the current member include an ICD-9 code corresponding to a mental health diagnosis. If an appropriate ICD-9 code is found in the claims data, a "yes" is entered in this field; if not, a "no" is entered. In another embodiment of the present invention, the entry for mental health diagnoses 72 is determined by examining the facility claims for the current plan member for an appropriate ICD-9 code. In another embodiment of the present invention, all medical claims for the current plan member are examined.

The entry for self-care characteristics 74 is also either a "yes" or a "no" entry. In one embodiment of the present invention, the appropriate entry for self-care characteristics 74 is determined by examining the present member's claims for an ICD-9 code corresponding to a diagnosis that represents some type of disability. Self-care characteristics 74 is used by the intervention agent to determine factors effecting provision of care. In one embodiment of the present invention, the self-care characteristics 74 searched for in the claims data includes hearing impairment, visual impairment, ambulatory impairment, and diabetes. In other embodiments of the present invention, more or fewer self-care characteristics are searched for in the claims data for the current plan member. In one embodiment of the present invention, the pharmacy claims are also searched for any self-care characteristics.

The entry for equipment or monitors 76 is also either a "yes" or a "no" entry. The proper entry is determined by examining the medical claims for the current member for a HCPC or CPT code for medical equipment or a monitoring device. If such a code is found, this entry is recorded as a "yes." Likewise, the pharmacy claims are examined for the presence of a code corresponding to appropriate durable medical goods. Again, if such a code is found, this entry is recorded as a "yes." Like the entry for self-care characteristics 74, the entry for equipment or monitor 76 is used to provide the intervention agent with information on the current plan member and with an entry point for discussion regarding whether the member is properly using the equipment or monitor. The entry for drug history 78 is also either a "yes" or "no" entry. The proper entry for drug history 78 is ascertained by examining the pharmacy claims for the current plan member to determine whether the member has been prescribed any medications. If the member has been prescribed medications, a "yes" is entered for drug history 78.

In one embodiment of the present invention, more information can be obtained on each of the entries shown in the "risk factors" section 66, shown on the left hand side of this section, by selecting the entry (e.g., by "clicking" on the entry). In one embodiment of the present invention, all of the risk factors 66, shown on the left hand side can be selected to obtain further information.

Figure 5:
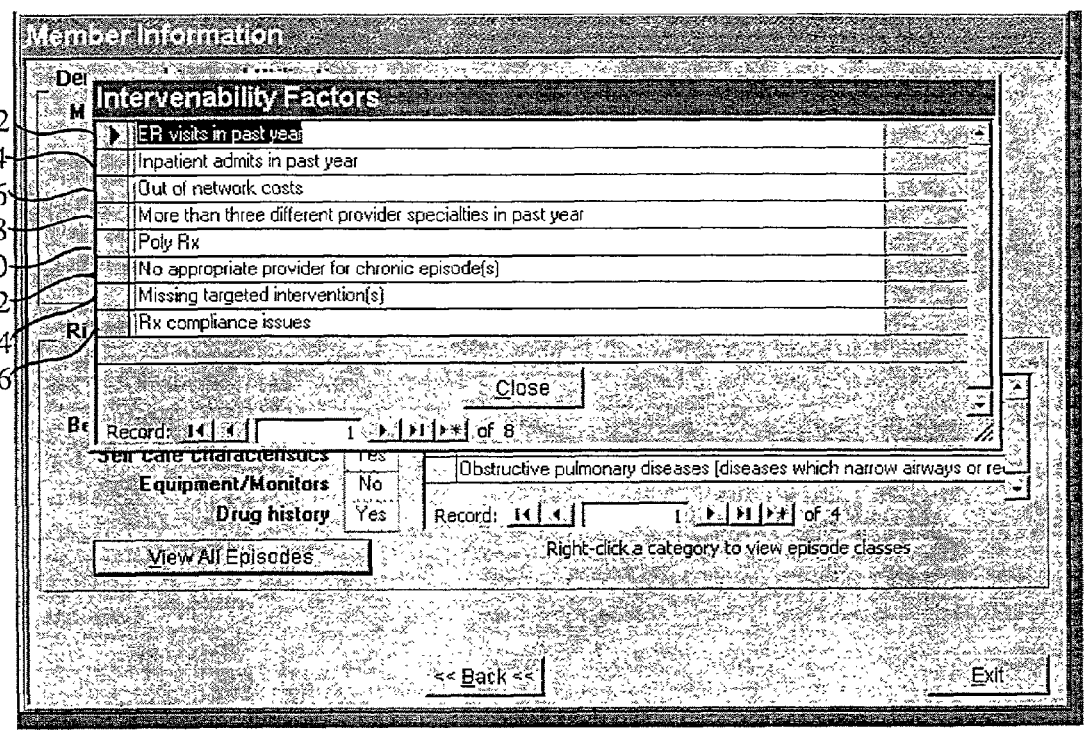
FIG. 5 shows an exemplary screen display of an intervenability factors screen for the current member, according to one embodiment of the present invention.

In one embodiment of the present invention, further information on the intervenability factors present for the current member can be obtained by selecting intervenability 70. FIG. 5 is a screen display showing an intervenability factors screen 80, according to one embodiment of the present invention. As shown in FIG. 5, the intervenability factors screen 80 provides a brief description of each of the intervenability factors present for the current member.

In one embodiment of the present invention, as shown in FIG. 5, possible intervenability factors that may be displayed on the intervenability factors screen 80 include whether the current plan member had any emergency room visits in the focus period (numeral 82), whether the current member had any in-patient hospital admissions within the focus period (numeral 84), whether the current member incurred any out-of-network costs (numeral 86), whether the current member had more than three different provider specialists within the focus period (numeral; 88), whether the current member had more than a specified number of pharmacy prescriptions (numeral 90), whether the member is seeing an appropriate health care provider for a chronic episode (numeral 92), whether the current member is missing any targeted interventions for medical diagnoses (numeral 94), and whether the current member is non-compliant with any prescriptions (numeral 96). Further information can be obtained on each of the intervenability factors shown on the intervenability factors screen 80 in FIG. 5, by selecting the desired intervenability factor. In other embodiments of the present invention, more or fewer intervenability factors are employed.

Whether the current plan member had any emergency room visits within the focus period (intervenability factor 82) is determined by examining the medical claims for the member to search for any codes in the claims indicating an emergency room visit. Further information can be obtained on intervenability factor 82 by selecting it, as described above. In one embodiment of the present invention, when intervenability factor 82 is selected, the medical claims indicating an emergency room visit by the plan member are displayed for further review by the intervention agent. While FIG. 5, describes this factor as "ER visits in past year," any time period (e.g., the focus period) may be examined in accordance with the present invention.

Whether the current plan member had any hospital admissions during the focus period (intervenability factor 84) is likewise determined by examining the medical claims for the plan member. This factor is identified as "inpatient admits in past year," in FIG. 5. If any of the medical claims include a code indicating that the member was admitted to a hospital or other appropriate health care facility, then intervenability factor 84 is present for the current member. The intervention agent may obtain further information on intervenability factor 84 by selecting it on the intervenability factors screen 80. In one embodiment, selecting intervenability factor 84 causes a display of the medical claims evidencing an in-patient hospital admission of the current plan member.

Whether the current plan member incurred any out-of-network costs (intervenability factor 86) is again determined by an examination of the member's medical and pharmacy claims. If any of the claims were submitted by providers that are not within the health care plan's network, the total costs are calculated and intervenability factor 86 is counted as present for the current member. In one embodiment of the present invention, if intervenability factor 86 is selected, the claims evidencing out-of-network costs for the member are displayed.

Whether the current plan member saw more than three different specialists in the focus period (intervenability factor 88) is again determined by examining the medical claims for the member. If the medical claims indicate that the member visited more than three providers during the focus period, intervenability factor 88 is counted as present for the current member. In one embodiment of the present invention, if the intervention agent selects intervenability factor 88, the claims showing the specialists seen by the member are displayed.

Whether the current plan member has been prescribed more than a specified number of medications (intervenability factor 90) is determined by an examination of the pharmacy claims for the member. This factor is identified as "Poly Rx," in FIG. 5. In one embodiment of the present invention, the intervenability factor 90 is counted as present for the current member if eight or more distinct medications are present in the pharmacy claims for that member. In another embodiment, the intervenability factor 90 is counted as present if more than one distinct medication is present for the member. By "distinct medications," it is meant that if a member has multiple prescriptions filled for the same medication, it will count as only one prescription for purposes of determining the presence of the intervenability factor 90. In other embodiments of the present invention, a greater or fewer number of distinct medications trigger the presence of the intervenability factor 90. In one embodiment of the present invention, when the intervention agent selects the intervenability factor 90, the pharmacy claims showing the distinct medication prescribed to the member are displayed.

Whether the current plan member is seeing an appropriate provider for a medical episode is the subject of the intervenability factor 92. In one embodiment of the present invention, intervenability factor 92 only examines chronic episodes, as chronic episodes provide a significant contribution to health care resource utilization. In another embodiment, all medical episodes are considered. In one embodiment of the present invention, the presence of the intervenability factor 92 is determined by searching the member's medical claims to determine whether a particular medical episode is present for the member. In one embodiment of the present invention, the medical episodes that are investigated under intervenability factor 92 are stored in a look-up table that can be easily used manually or by a software program. In one embodiment of the present invention, the particular medical episodes that are investigated are specified by CCG classes or categories. A skilled healthcare practicioner can readily identify medical episodes and corresponding healthcare providers that are amenable to examination.

In one embodiment of the present invention, for example, the medical episodes investigated include otitis media (e.g., middle ear infection) and pregnancy. The look-up table also includes a list of one or more providers corresponding to each of these medical episodes. For example, the corresponding providers for pregnancy include an obstetrician, a family practice physician, or an internist. If the medical claims for the current member indicate a pregnancy, the physician claims are searched to verify that an obstetrician, a family practice physician, or an internist is managing the member. If one of the specified medical episodes is present for the current member, and the member has failed to see an appropriate physician, the intervenability factor 92 is counted as present for the current member. In one embodiment of the present invention, the intervention agent can obtain further information on the intervenability factor 92 by selecting it on the intervenability factor screen 80. If the intervenability factor 92 is selected, the medical claims corresponding to the medical episode for which the plan member has failed to visit an appropriate provider are displayed.

Whether the current plan member has aspects of care for a specified disease meriting intervention (intervenability factor 94) is addressed in a similar manner as that described with respect to intervenability factor 92. This factor is identified as "missing targeted interventions," in FIG. 5. Medical episodes or conditions of interest are specified in conjunction with corresponding interventions. A healthcare provider (e.g., a physician) having ordinary skill in the art, based on his or her knowledge and experience, can readily perform this specification. In one embodiment of the present invention, for example, the conditions that are investigated include diabetes, heart failure, asthma, and chronic obstructive pulmonary disease ("COPD"). In other embodiments of the present invention, other medical conditions may also be analyzed under this intervenability factor. Again, a skilled medical practitioner can specify corresponding interventions. In one embodiment, the medical episodes are specified using CCG class or categories.

If it is determined that the current plan member has diabetes, for example, the medical and pharmacy claims for the member are examined to determine whether that member is seeking certain types of treatment that should be associated with diabetes, as identified by procedural and pharmacy codes in the claims. In one embodiment of the present invention, there are separate treatment protocols, one for insulin-dependent diabetes and one for non-insulin-dependent diabetes. In the case of insulin-dependent diabetes, the treatments that are searched for include whether the member is receiving insulin, whether the member is receiving an annual eye exam, whether the member is receiving a hemoglobin test and whether the member is visiting an endocrinologist. If any of these conditions corresponding to insulin-dependent diabetes is missing from the member's claims, the intervenability factor 94 is counted as present for the current member. This same process is applied for all specified medical conditions. Also, for example, if the member is diagnosed with heart failure, pharmacy claims are examined to verify that the member is filling prescriptions for ACE-inhibitors. If the member's pharmacy claims do not indicate a fill of this prescription, the intervenability factor 94 is indicated as present for the member. In one embodiment of the present invention, the intervenability factor 94 is examined using a table including a list of medical conditions of interest in one column, and including a list of corresponding medications in another column.

Figure 6:
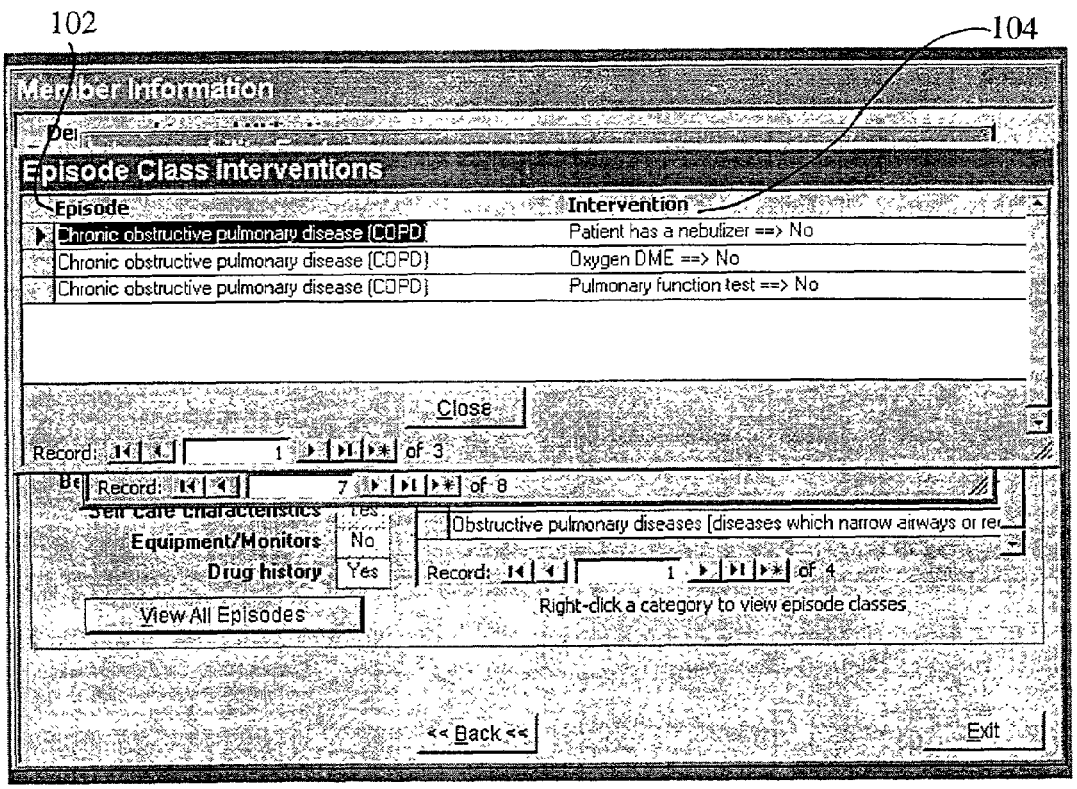
FIG. 6 shows an exemplary screen display of an episode class intervention screen for the current member, according to one embodiment of the present invention.

In one embodiment of the present invention as shown in FIG. 6, the intervention agent can obtain further information on the intervenability factor 94 by selecting it on the intervenability factors screen 80. FIG. 6 shows a display of an episode class interventions screen 100, according to one embodiment of the present invention. The episode class intervention screen 100 provides the intervention agent with additional information regarding the treatments or interventions for a member having a diagnosis of COPD in the claims. As shown in FIG. 6, an episode of COPD causes the method of the present invention to search for whether the member has a nebulizer (found in the member's pharmacy claims), whether the member has had an oxygen DME (found in the member's medical claims), and whether the member has had a pulmonary function test (found in the member's medical claims). The episode class intervention screen 100 provides a "yes" or "no" indication for each to the intervention agent for each of these interventions. As shown in FIG. 6, the episode class intervention screen 100 includes an episode 102 column and an intervention 104 column. In one embodiment of the present invention, the episodes are specified in terms of CCG classes, categories, or specialties, using the Ingenix CCG system described above. In another embodiment of the present invention, the episodes are specified using ICD-9 codes. Use of CCG's or ICD-9 codes facilitates the method of the present invention in searching the claims for the member.

Whether the current plan member is compliant with taking prescribed medications (intervenability factor 96) is determined by examining the pharmacy claims for the member. This factor is identified as "Rx compliance issues," in FIG. 5. In one embodiment, the pharmacy claims are examined for the presence of medications that are generally prescribed for chronic conditions or are generally taken over a long term. The pharmacy claims are also examined for any medication for which treatment duration is known or is typical. If such a medication is found in the member's pharmacy claims, they are further examined to verify that the member has continued to fill the prescription over the entire time of the focus period, or at least over the normal required time associated with the medication. Examples of medications for which if they are filled once normally be filled throughout the focus period include insulin, asthma inhalers, and ACE-inhibitors. If the current member has a pharmacy claim for one of these medications during the focus period and fails to continue to fill the prescription throughout the period, intervenability factor 96 is indicated as present for the member. If the intervenability factor 96 is shown on the intervenability factors screen 80 in FIG. 5, the intervention agent can obtain further information by selecting it.

In one embodiment of the present invention, medication compliance is analyzed for the current member by examining all medications having at least two fills indicated by the member's pharmacy claims. For each medication appearing at least twice, a formula is applied using the fill dates and the fill durations (e.g., 30 days, 60 days, 90 days, etc.) to determine whether the member is compliant with that particular medication. For example, if the current member's pharmacy claims show that Medication A was filled three times, each time spaced 90 days from the previous fill, and each fill was for a duration of 30 days, the formula will indicate that intervenability factor 90 is present for the member.

Figure 7:
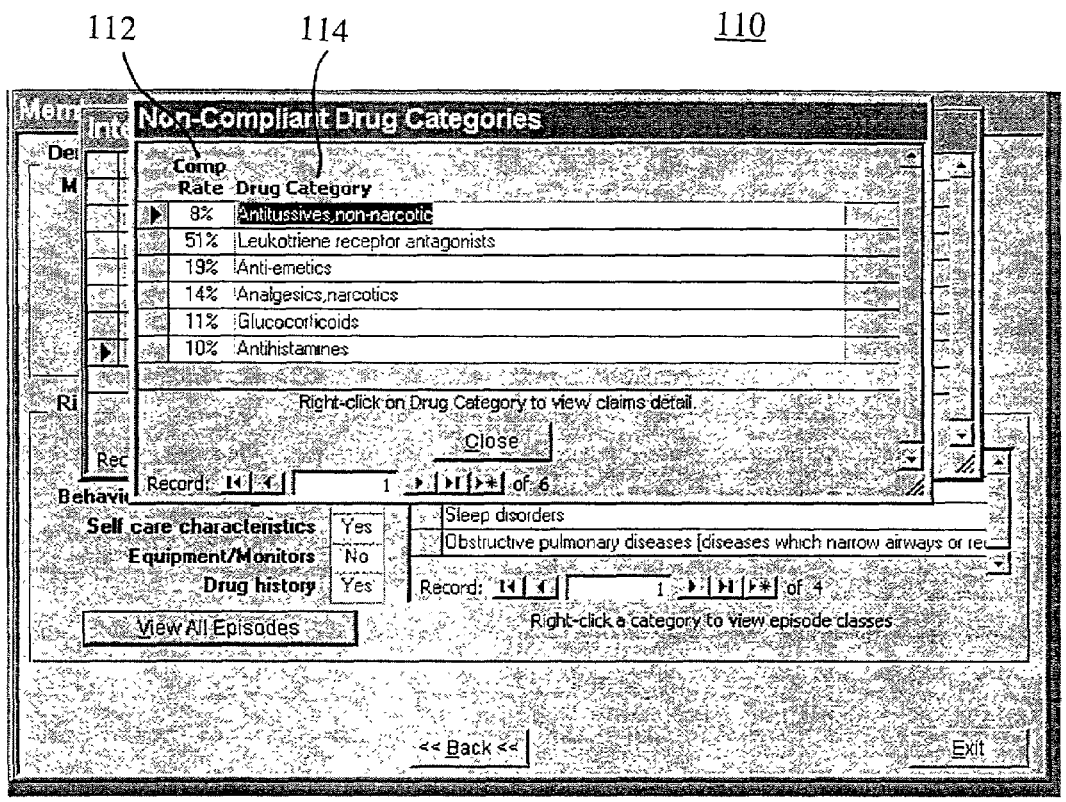
FIG. 7 shows an exemplary screen display of a non-compliant drug categories screen, according to one embodiment of the present invention.

FIG. 7 shows a display of a non-compliant drug categories screen 110, according to one embodiment of the present invention. As shown in FIG. 7, the non-compliant drug category screen 110 includes a column for compliance rate 112 and a column for drug category 114. In one embodiment of the present invention, the compliance rate is a percentage indicating the percent of times the member filled a prescription for a particular medication. The drug category 114 indicates the particular medication that the member is not filling. In one embodiment of the present invention, the drug categories are determined using National Drug Code ("NDC") categories. In another embodiment of the present invention, more general drug categories including multiple NDC's are used.

While eight intervenability flags are identified above, a healthcare practitioner having ordinary skill in the art may readily identify other appropriate intervention flags signaling that a member is amenable to intervention in care by an intervention agent. For example, a member's claims can readily be examined for compliance with specified physician practice patterns relating to treatment of a specified disease or medical condition.

Figure 8:
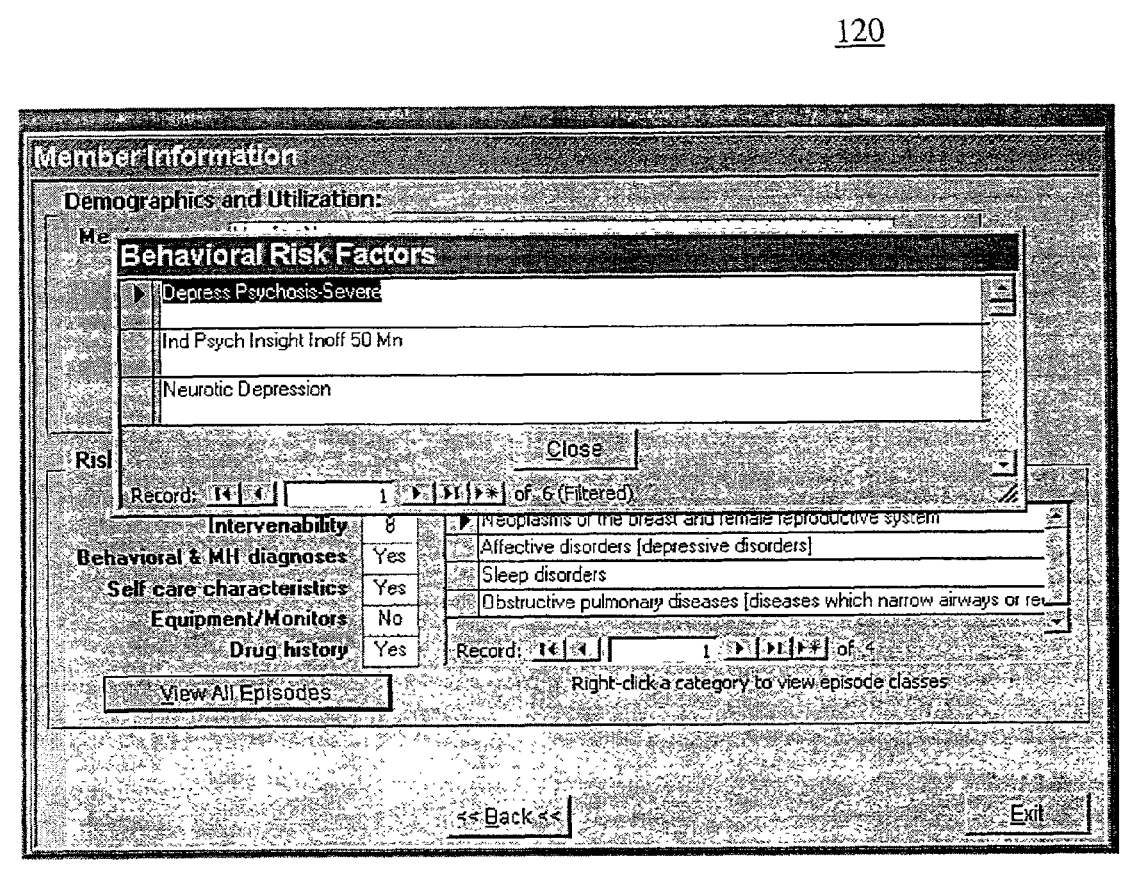

The next factor, shown in the "risk factors" section 66 on the member information screen 60 in FIG. 4 is mental health diagnoses 72. As described above, the intervention agent can obtain additional information by selecting this entry. FIG. 8 shows a display of additional information regarding this category in a behavioral risk factors screen 120. In the embodiment shown in FIG. 8, the behavioral risk factors screen 120 includes a list of each of the behavioral or mental health diagnoses present in the claims of the current plan member. The presence of behavioral or mental health diagnoses is ascertained by examining both the medical claims and the pharmacy claims for the member for ICD-9, CPT, HCPC, or NDC codes corresponding to mental health diagnoses. In one embodiment of the present invention, only one of the categories of medical claims and pharmacy claims is examined. In one embodiment of the present invention, the method involves examining the claims for the presence of a specified code or set of codes corresponding to behavioral or mental health diagnoses. In one embodiment of the present invention, the intervention agent, may access further information on one of the behavioral risk factors by selecting it on the behavioral risk factors screen 120. If the intervention agent selects the behavioral risk factor, the corresponding medical and pharmacy claims will be displayed.

The next risk factor, shown in the "risk factors" section 66 on the member information screen 60 is self-care characteristics 74. The intervention agent may obtain further information on this category by selecting it. If the intervention agent selects self-care characteristics 74, the corresponding claims for the member from the claims database will be displayed. The next risk factor 66 shown is equipment or monitors 76. By selecting this category, the intervention agent can access the claims corresponding to equipment or monitors for the current member. The final risk factor 66 shown is drug history 78. By selecting this category, the intervention agent can obtain a link to each of the pharmacy claims for the member.

FIG. 9 shows a drug history report screen 130 according to one embodiment of the present invention. As shown in FIG. 9, the drug history report includes a column for drug category 132, fill date 134, NDC code 136, and drug name 138. An intervention agent may use the drug history report 130 shown in FIG. 9 to further assess the current member's health care situation and any necessary interventions.

The right hand side of the "risk factors" section 66 is a listing of top medical episode categories 79. This listing (briefly described above) is intended to provide the intervention agent with summary information regarding the current member's primary medical conditions driving the member's risk and health care resource utilization. In one embodiment, this listing is generated by examining the current member's medical claims to determine which medical episode has the highest associated cost. In one embodiment, the medical episodes are organized according to CCG classes or categories, as described above. In another embodiment, the episode categories are organized by specified groups of ICD-9 codes, or by individual ICD-9 codes. In another embodiment of the present invention, this listing is generated by searching the member's medical claims to determine the presence of various CCG categories for the member. Next, a predetermined ranking of CCG categories is used to identify those considered to be high risk categories. In this embodiment, each of the CCG categories is assigned a ranking by associated risk. The top risk CCG categories for a given plan member are then listed in the top medical episode categories 79. In this embodiment, the ranking of the CCG categories is done according to historical experience. A person skilled in the art can assign a risk or health care resource utilization ranking to a CCG category based on their knowledge and experience with that particular medical episode.

In another embodiment of the present invention, each CCG category is assigned an average cost by examining a base set of claims for an historical time period, and calculating the average cost associated with each CCG category. This average cost is then used as the ranking for each CCG category. In another embodiment of the present invention, the listing in categories 79 is determined by using a combination of the costs associated with the particular CCG category for the current member, and the average historical costs associated with the CCG category, using an appropriate formula. In this embodiment, a first ranking is assigned to each CCG category present based on the member's particular cost and a second ranking is assigned to each CCG category present based on the average historical costs. The first and second rankings are then summed together to reach an overall ranking for each CCG category. In one embodiment, the top five CCG categories for the member are displayed in the top medical episode categories 79.

In one embodiment of the present invention, the intervention agent can obtain further information on any of the listed medical episodes by selecting it. If the intervention agent selects an episode, the member's episodes for that CCG category will be displayed by CCG class. In one embodiment, if the intervention agent then selects one of the displayed CCG classes, a breakdown of that CCG class is displayed by summarizing claims in three categories: (1) emergency room visits, (2) in-patient admissions, (3) specialist care, and (4) pharmacy cost. If one of these categories is selected, the claims corresponding to that category will be displayed. In another embodiment, the intervention agent may cause the corresponding claims to be displayed by selecting the displayed medical episode.

In one embodiment, the method of the present invention operates using the following sequence of steps. First, a predicted total cost and a relative risk are calculated for each member of a group. Next, the members of the group are ranked by each member's relative risk and a high-risk group of members is chosen by choosing member's from the group having the highest relative risk. In one embodiment, the top three to five percent of the member's are chosen as the high-risk members. Next, the corresponding claims for each of the high-risk members are examined to identify intervention flags, top medical episodes driving risk, and care influencing factors. Next, a high-risk database is compiled containing information on each of the high-risk members. This information includes the items specified above and a complete claim detail history.

A set of intervention members is then selected from the high-risk members. The selection is done on a member intervention application using one or a combination of the following criteria: relative risk, relative risk rank, presence of a disease category, and demographic information. Next, the member intervention application displays a list of the intervention members to an intervention agent. Finally, the intervention agent selects one of the intervention members for display, and the member intervention application displays the above-identified information corresponding to the selected intervention member.

Using the member information screen 60, the intervention agent can quickly obtain relevant and useful information regarding a member's medical treatment history and use that information to contact the member and proactively intervene in the member's care by providing guidance and suggestions for improving that care.

Although the present invention has been described with reference to preferred embodiments, persons skilled in the art will recognize that changes may be made in form and detail without departing from the spirit and scope of the invention.

I claim:

1. A computer-implemented high risk member identification method, comprising a computer performing the following:
    identifying a group of members to be analyzed using a computer software application, each group member having an associated relative risk value, wherein the relative risk value for each member is a function of predicted future healthcare resource utilization for the member;
    filtering the group members using the computer software application to identify members having an associated relative risk value that exceeds a threshold value of relative risk, thereby identifying a subset of the group members for potential intervention;
    creating a database of claim data for the subset members, wherein the database includes all medical diagnoses and healthcare utilization patterns for each subset member during a focus period, including any physician claims, facility claims and pharmacy claims associated with each subset member during the focus period;
    analyzing the claim data of each subset member using the computer software application to ascertain the presence or absence of each of a plurality of intervenability factors present to the subset member, wherein the intervenability factors for each subset member are identified based upon aspects of each subset member's care history that are amenable to intervention by an intervention agent, and wherein the intervenability factors include: (a) whether the member visited the emergency room during the focus period, (b) whether the member had any in-patient hospital admissions during the focus period, (c) whether the member incurred any out-of-network costs during the focus period, (d) whether the member visited more than three different provider specialists during the focus period, (e) whether the member was prescribed multiple pharmaceuticals during the focus period, (f) whether the member has no appropriate provider for a chronic episode during the focus period, (g) whether the member missed a target intervention during the focus period, and (h) whether the member fails to obtain fills of prescribed medication during the focus period;
    using the computer software application to assign each subset member a number of intervenability factors representing a total number of the intervenability factors present in the subset member's claim data;
    using the computer software application to assign a relative risk ranking to each subset member based upon the subset member's associated relative risk value and the number of intervenability factors assigned to the subset member;
    using the computer software application to determine one or more top medical episodes driving risk of each subset member, wherein the top medical episodes are determined by examining the subset member's claim data by diagnosis code or medical episode to determine which of the subset member's medical conditions has the highest associated cost;
    displaying (a) a list of the subset members ordered by respective relative risk rankings and (b) the relative risk value for each subset member on an electronic display;
    receiving a selection of one or more displayed subset members input into the computer software application by an intervention agent; and
    displaying demographic information, a utilization summary, risk factors including behavioral risk factors and self-care characteristics, the intervenability factors, and the one or more top medical episodes for each subset member selected by the intervention agent on the electronic display.

2. The method of claim 1, wherein the intervention agent may filter the displayed subset members by zipcode, county, group numbers, products, member ID or member names.

* * * * *

UNITED STATES PATENT AND TRADEMARK OFFICE
CERTIFICATE OF CORRECTION

PATENT NO. : 7,640,175 B1  
APPLICATION NO. : 09/733215  
DATED : December 29, 2009  
INVENTOR(S) : Prasad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this

Twenty-first Day of December, 2010

David J. Kappos  
*Director of the United States Patent and Trademark Office*